United States Patent [19]
Kinoshita

[11] Patent Number: 5,193,910
[45] Date of Patent: Mar. 16, 1993

[54] THERMAL ANALYSIS INSTRUMENT

[75] Inventor: Ryoichi Kinoshita, Tokyo, Japan

[73] Assignee: Seiko Instruments, Inc., Tokyo, Japan

[21] Appl. No.: 786,112

[22] Filed: Nov. 4, 1991

[30] Foreign Application Priority Data

Nov. 2, 1990 [JP] Japan .................................. 2-298205

[51] Int. Cl.⁵ ............................................ G01N 25/00
[52] U.S. Cl. ........................................ 374/45; 165/27; 374/11; 374/57
[58] Field of Search .................. 374/10, 11, 12, 45, 374/57

[56] References Cited

U.S. PATENT DOCUMENTS

| | | | |
|---|---|---|---|
| Re. 32,625 | 3/1988 | Schwarz | 374/57 |
| 4,575,257 | 3/1986 | Ogura et al. | 374/45 |
| 4,711,433 | 12/1987 | Goto | 266/87 X |
| 4,781,358 | 11/1988 | Langan | 266/87 X |
| 4,787,752 | 11/1988 | Fraser et al. | 374/57 X |

OTHER PUBLICATIONS

"High Temperature Cell" Dupont Thermal Analysis Bulletin No. 900-7, Feb. 1965, (4 pages).

*Primary Examiner*—Daniel M. Yasich
*Attorney, Agent, or Firm*—Spensley Horn Jubas & Lubitz

[57] ABSTRACT

A thermal analysis instrument which is equipped with a cooling mechanism and device for blowing a drying gas so that when low temperature are being measured moisture is prevented from condensing on the upper end surface of the heating furnace and on a cover that closes the inside of the heating furnace to thereby prevent deposition of frost. Where a robot mechanism is added to this thermal analysis instrument equipped with the cooling mechanism, it is not necessary to impose additional functions on the robot mechanism. The device for blowing a drying gas presents an annular passage mounted near the upper end surface of the heating furnace for blowing the drying gas against the upper end surface and the cover to thereby prevent the deposition of frost.

13 Claims, 3 Drawing Sheets

THERMAL ANALYSIS INSTRUMENT

BACKGROUND OF THE INVENTION

This invention relates to improvements in thermal analysis instruments equipped with a cooling mechanism.

A conventional thermal analysis instrument equipped with a cooling mechanism is disclosed in Japanese Patent Application Laid-Open No. 116744-02 and has a structure as shown in FIG. 6 of the drawings of the present application. In particular, the thermal analysis instrument, in particular a differential scanning calorimeter or a differential thermal analyzer, includes a controller 1 coupled to a heating furnace 2. A housing 11 of heat insulating material is formed around the sides of heating furnace 2 to form a closed space 8 between housing 11 and the sides of furnace 2. Cool air 54 is admitted into this chamber 11 and heated air 57 leaves chamber 11 via a passage 55. An opening is formed at the upper end of heating furnace 2 to permit a sample to be inserted into and withdrawn from furnace 2. A removable cover or the like is frequently put in this opening.

This cover or the like is installed to form a closed space around the sample placed inside heating furnace 2 to prevent the sample from being affected or disturbed by the outside air during measurements.

In recent years, some analysis instruments of this kind have often been equipped with a robot mechanism such as an automatic sampler to automate replacement and placement of samples. Numerous samples are successively subjected to measurement automatically.

Especially where a robot mechanism of this type is mounted to a thermal analysis instrument to attain automation, it is inevitable that a cooling mechanism is mounted to the heating furnace 2, because it is necessary to elevate and lower the temperature of the sample.

The heating furnace 2 of the conventional thermal analysis instrument equipped with a cooling mechanism has an open top portion and, therefore, the aforementioned robot mechanism such as an automatic sampler is especially adapted to be mounted to the instrument, for replacement and placement of the sample.

When a measurement is made with the instrument of this structure using a cooling refrigerant, if the temperature at the upper end of the heating furnace 2 becomes lower than the dew point of the atmosphere around the top portion of the furnace 2, then dew condensation occurs at the upper end portion of the furnace, because the upper end portion is in contact with the atmosphere.

Dew condensation takes place as long as the upper end of the heating furnace 2 is in contact with the open atmosphere. More dew condensation occurs as the temperature inside the furnace 2 drops, as the furnace 2 is kept at low temperatures for a longer time, and as the moisture content of the atmosphere increases, i.e. as the dew point increases.

When the temperature at the upper end structure of the heating furnace is low, the dew produced by the condensation becomes frost and deposits at the upper end of the furnace 2.

After a measurement, the robot mechanism removes the cover or the like placed at the upper end of the heating furnace 2 to replace the sample. At this time, the cover or the like and the opening at the upper end of the furnace 2 become frozen because of the frost deposited at the upper end of the furnace 2, including the cover or the like. This makes it impossible to remove the cover or the like.

Where it is essential for measurement that the temperature inside the heating furnace 2 be lowered, it is customary to add a closed space to the vicinities of the top portion of the furnace 2 to prevent the top portion of the furnace 2 from touching the open air, for preventing deposition of frost due to the aforementioned dew condensation.

In this case, however, if a robot mechanism is added to the instrument, it is necessary to open the added closed space by operation of the robot mechanism during replacement of the sample. Hence, a new function must be imparted to the robot mechanism. This represents a decided drawback.

SUMMARY OF THE INVENTION

It is an object of the present invention to provide a thermal analysis instrument which is equipped with a cooling mechanism and which prevents dew condensation on the upper end surfaces during measurements of low temperatures to thereby prevent deposition of frost. Where a robot mechanism is added to the instrument, it is not necessary that the robot mechanism be capable of performing further functions in addition to the essential functions which include placement and removal of the cover or the like and replacement of the sample.

Other and further objects, features and advantages of the invention will appear more fully from the following description.

The present invention has been developed to achieve the above-described objects. The novel instrument according to the invention comprises: a heating furnace; an annular drying gas passage mounted near the upper end surface of the heating furnace; an inlet port for introducing drying gas into the annular passage; and a discharge port which permits the drying gas introduced from the gas inlet port to be discharged into the outside air from the annular passage through the vicinities of the upper end surface of the furnace.

The above-described structure operates as follows. A drying gas is introduced from the drying gas inlet port and passed through the annular passage. Then, the gas passes by the upper end surface of the heating furnace and is discharged into the outside air. Thus, the dew point around the upper end surface of the heating furnace is lowered.

DESCRIPTION OF THE PREFERRED EMBODIMENTS

Figure 1:
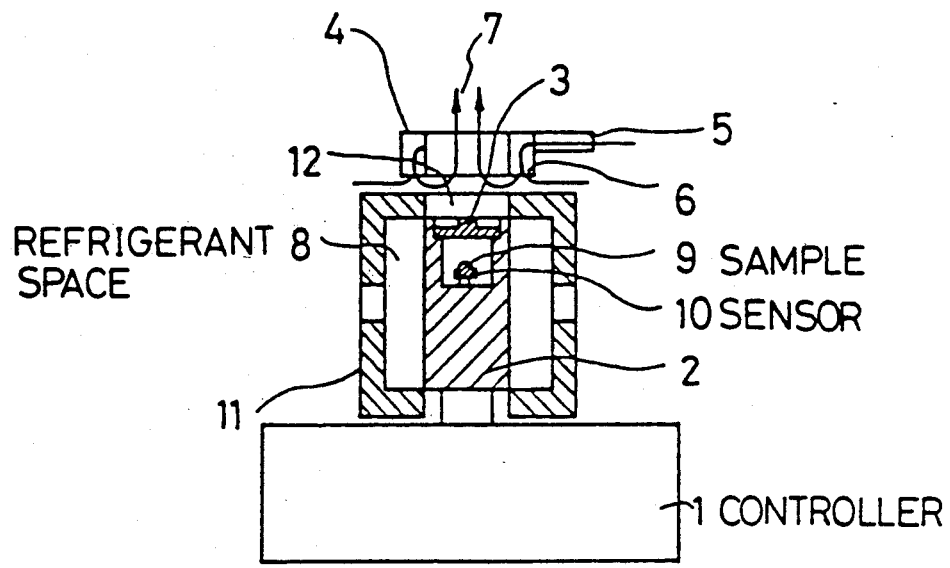
FIG. 1 is an elevational cross-sectional view of a first embodiment of an analysis instrument according to the invention.

FIG. 1 shows the whole structure of a first embodiment of the novel thermal analysis instrument of the invention. The instrument has a control portion, or controller, 1 for controlling the furnace temperature. A heating furnace 2 forms a part of the instrument. A sensor 10 is installed inside heating furnace 2 and a sample 9 is placed on sensor 10. A cover 3 is mounted at the upper end of furnace 2 to close to a sample introduction opening 12 at the upper end of furnace 2 and to isolate the space around sample 9 from the outside air, i.e. for creating a closed space, after a sample 9 has been placed inside furnace 2. In order to replace sample 9, cover 3 is removed.

A member 4, in the form of a cap, providing an annular gas passage is mounted above the upper end surface of furnace 2. Member 4 is provided with an inlet port 5 for introducing a drying gas into one side of the annular gas passage. The lower boundary of the annular gas passage in member 4 is open and forms a discharge port 6 for discharging the drying gas introduced via port 5. The flow of the drying gas through the annular gas passage is indicated by arrows 7. A refrigerant for cooling heating furnace 2 passes through a closed space 8 which is surrounded by a housing 11 of heat insulating material surrounding the sides of heating furnace 2.

Figure 2:
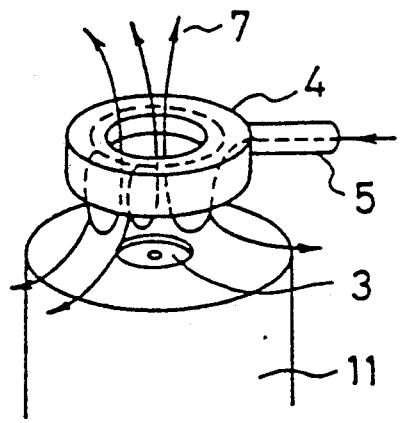
FIG. 2 is a perspective view of the top portion of the embodiment shown in FIG. 1.
Figure 3:
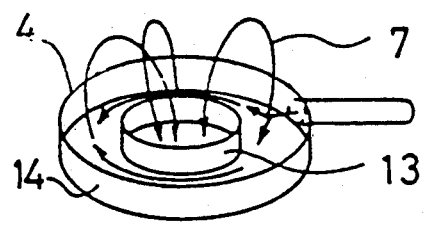
FIG. 3 is a perspective view of the annular gas passage of the embodiment of FIG. 1, as viewed from the bottom.

FIG. 2 is a perspective view showing the top portion of the first embodiment, viewed from above. FIG. 3 is a perspective view of member 4 of the first embodiment of the invention, as viewed from the bottom of that member.

In the operation of the first embodiment, as shown in FIG. 1, the heating furnace 2 is cooled by the refrigerant (not shown) passing through the closed space 8 which is formed for the passage of the refrigerant. At the same time, the temperature inside the furnace 2 is controlled by the controller. The sensor 10 inside the furnace 2 detects the temperature and thermal characteristics of the sample 9. The member 4 providing the annular gas passage is mounted above and near the upper end surface of heating furnace 2. The drying gas is admitted via inlet port 5 for the drying gas.

The inside diameter of the annular passage in member 4 is made larger than the outside diameter of cover 3. Thus, member 4 presents a central through passage via which cover 3 can be easily removed.

As shown in FIG. 3, the bottom of the annular gas passage in member 4 is fully open. The whole of this portion forms the discharge port 6 for the drying gas.

The drying gas introduced via the inlet port 5 for the gas collides against an inner wall 13 of member 4, delimiting the inner periphery of the annular gas passage, and flows along the inner wall 13, i.e., follows an annular path. The gas always flows out of the annular passage toward the bottom, i.e., downwardly, via the discharge port 6 for drying gas. Drying gas is introduced to inlet port 5 at a rate sufficient to maintain a low dew point in the atmosphere outside of the heating furnace and adjacent the sample introduction opening to substantially prevent frost from forming in the heating enclosure at the location of the sample introduction opening.

In FIGS. 1 and 2, the drying gas discharged from the discharge port 6 of the annular gas passage provided by member 4 flows downwardly. Then, some of the gas passes over the cover 3 and discharges into the outside air via the through passage at the center of member 4, which through passage is surrounded by the annular gas passage provided by member 4. Also, some drying gas passes by the upper end surface of heating furnace 2, escapes laterally, and discharges into the outside air.

Thus, it follows that the drying gas constantly flows by the upper end surface of the heating furnace 2, i.e., flows above and near the cover 3, and discharges into the outside air. That is., the atmosphere around the upper end surface of furnace 2 is constantly replaced. Therefore, any moisture in the atmosphere existing around the upper end surface of furnace 2 is continuously discharged into the outside air. Consequently, the dew point around the upper end surface of furnace 2 is lowered and maintained at a low level.

Deposition of frost on the cover 3 mounted on the upper end surface of the heating furnace 2 does not take place, unlike in the prior art techniques. Also, freezing occurs neither on the cover 3 nor around the opening of the upper end of the furnace 2. Therefore, it is unlikely that the cover 3 cannot be removed.

If cover 3 is to be removed by a robot mechanism, the removal can be effected via the through passage in member 4. It is thus not necessary to add any new mechanism for robot removal and replacement of cover 3.

Figure 4:
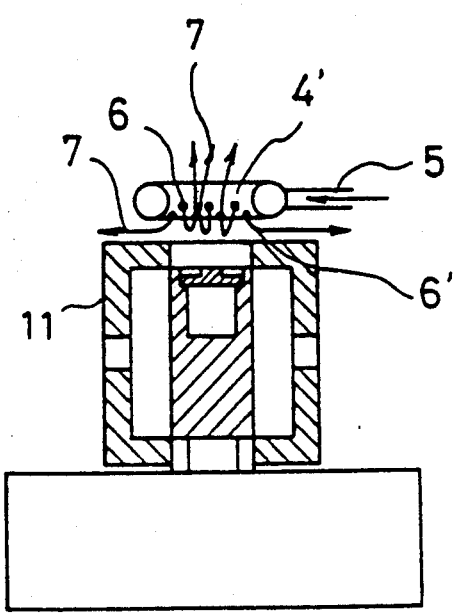
FIG. 4 is a view similar to that of FIG. 1 of a second embodiment of an analysis instrument according to the invention.

FIG. 4 shows the structure of a second embodiment of the invention, and in which the annular fluid passage is formed by a circular section of pipe 4'.

This embodiment has a thermal analysis instrument, a heating furnace, etc. which are similar to the counterparts of the first embodiment of FIG. 1. The inside diameter of the annulus defined by pipe 4' is selected to permit passage of cover 3.

The ring-shaped pipe 4' is mounted slightly above the upper end surface of the heating furnace 2, in the same way as in the first embodiment, and also slightly above the upper surface of housing 11. A plurality of holes defining dry gas discharge ports 6, are formed in the wall of pipe 4' in the region of the lower boundary and the lower part of the inner periphery of the annular gas passage provided by pipe 4'. Drying gas introduced via drying gas inlet port 5 passes through the annular gas passage in pipe 4' and is discharged to the region just above cover 3 via drying gas discharge ports 6'.

The discharged drying gas replaces the atmosphere near and above cover 3 as indicated by arrows 7 in FIG. 4. Some of the gas passes through the through passage enclosed by pipe 4' and discharges into the outside air. Some of the gas escapes horizontally and radially outwardly beneath pipe 4' and the discharges into the outside air.

Obviously, also in the second embodiment, the dew point near and above cover 3 is maintained low, in the same way as in the first embodiment.

Figure 5:
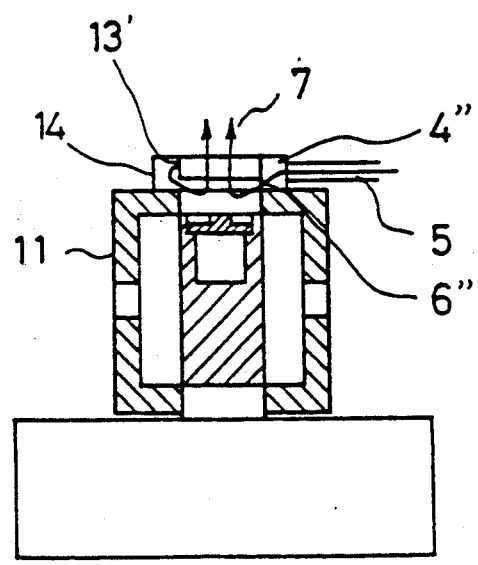
FIG. 5 is a view similar to that of FIG. 1 of a third embodiment of an analysis instrument according to the invention.
Figure 6:
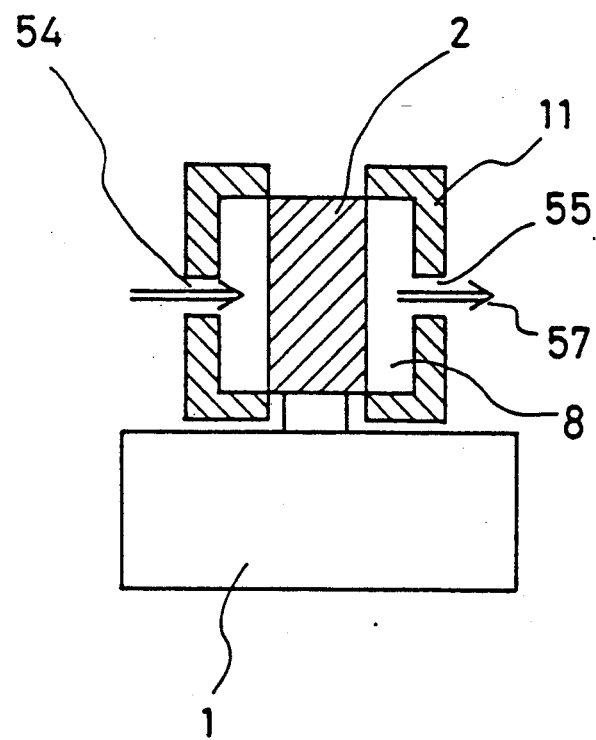
FIG. 6 is a view similar to that of FIG. 1 of an analysis instrument according to the prior art.

FIG. 5 shows the structure of the third embodiment of the invention. In this embodiment, a cap 4'' providing an annular fluid passage is integral with housing 11 of heat insulating material, which surrounds heating furnace 2. Cap 4''0 is constituted by an outer circular wall 14 and an inner circular wall 13' which delimit the outer and inner boundaries of the annular passage provided by cap 4''. The lower edge of wall 13' is located at a higher elevation than the lower edge of wall 14. Cap 4'' is mounted on housing 11 by fastening the lower edge of wall 14 to the upper surface of housing 11.

A discharge port 6'' for the drying gas is constituted formed by a gap created between the lower edge of inner wall 13' and the upper surface of housing 11.

Drying gas introduced via inlet port 5 enters and flows around the annular gas passage in cap 4", and is then discharged from the annular passage via discharge port 6". The drying gas which exits via discharge port 6" replaces the atmosphere near and above cover 3, and then flows through the through passage enclosed by cap 4" and discharges into the outside air above cap 4".

Obviously, also in the third embodiment, the dew point in the region above and near cover 3 is maintained at a low level, in the same way as in the first and second embodiments.

In these embodiments, the inlet port for the drying gas is mounted at only one location about the circumference of the annular gas passage. It is obvious that the same advantages as those offered by the illustrated embodiments can be obtained if a plurality of inlet ports are provided.

Further, in these embodiments, in which the drying gas is passed through the annular gas passage, it is obvious that the drying gas can be directed against the upper end surface of the furnace 2 via a nozzle or nozzles associated with the gas discharge passages.

As described thus far, in accordance with the present invention, the novel thermal analysis instrument equipped with a cooling mechanism has a ring-shaped fluid passage or the like for a drying gas near the upper end surface of the heating furnace of the instrument. The drying gas constantly flows along the cover installed on the upper end surface of the heating furnace and discharges into the outside air. The surroundings of the cover are kept dry, i.e., the dew point is kept low. Therefore, if the upper end surface of the furnace is cooled during measurement of low temperatures, deposition of frost in the vicinities of the cover is prevented. This, in turn, prevents freezing of the opening at the upper end surface of the furnace; otherwise the cover could not be removed.

Since the fluid passage for drying gas is given an annular form and the cover is permitted to pass inside the annulus, it is not necessary to add any function other than the indispensable functions, i.e. removal of the cover and replacement of the sample, when the sample is replaced by a robot mechanism.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. In a thermal analysis instrument comprising:
    a heating furnace defining a heating enclosure having a sample introduction opening, the furnace being operative for heating a sample placed in the heating enclosure to a given temperature;
    a cover for covering said sample introduction opening in order to close said heating enclosure;
    a controller connected to control the temperature inside said heating furnace; and
    a sensor for detecting the temperature of a sample inside said heating enclosure; the improvement comprising
    blowing means for blowing a drying gas against said heating furnace in the vicinity of said sample introduction opening.

2. A thermal analysis instrument as claimed in claim 1 wherein said heating furnace has an upper end at which said sample introduction opening is located, and said blowing means define an annular gas passage located near said upper end of said, heating furnace and has at least one discharge port communicating with said annular gas passage for discharging drying gas into the outside air.

3. A thermal analysis instrument as claimed in claim 2 wherein said blowing means further have an inlet port communicating with said annular gas passage for introducing drying gas into said annular gas passage.

4. A thermal analysis instrument as claimed in claim 3 wherein said blowing means comprise outer and inner circular walls delimiting outer and inner peripheral boundaries of said annular gas passage.

5. A thermal analysis instrument as claimed in claim 4 wherein said blowing means have a side which faces said heating furnace and said annular gas passage is open at said side to define said discharge port.

6. A thermal analysis instrument as claimed in claim 4 wherein said inner circular wall of said blowing means has a lower edge which faces toward said furnace and said inner circular wall is dimensioned so that said lower edge defines a side of said discharge port.

7. A thermal analysis instrument as claimed in claim 3 wherein said blowing means comprise a hollow pipe in the form of a ring.

8. A thermal analysis instrument as claimed in claim 7 wherein said pipe is provided with a plurality of holes defining discharge ports.

9. A thermal analysis instrument as claimed in claim 8 wherein said holes are directed radially inwardly of said annular gas passage and toward said furnace.

10. A thermal analysis instrument as claimed in claim 2 wherein said blowing means present a through passage which is surrounded by said annular gas passage and which has a cross section which is dimensioned to permit said cover to traverse said through passage.

11. A thermal analysis instrument as claimed in claim 1 further comprising a housing of heat insulating material surrounding said heating furnace and having an outer surface which is spaced from said sample introduction opening of said heating furnace, and said blowing means are mounted on said outer surface of said housing.

12. A thermal analysis instrument as claimed in claim 1 further comprising means for supplying to said blowing means a drying gas at a rate sufficient to maintain a low dew point in the atmosphere outside of said heating furnace and adjacent said sample introduction opening.

13. A method of operating a thermal analysis instrument, which instrument includes:
    a heating furnace defining a heating enclosure having a sample introduction opening, the furnace being operative for heating a sample placed in the heating enclosure to a given temperature;
    a cover for covering the introduction opening in order to close the heating enclosure;
    a controller connected to control the temperature inside the heating furnace; and a sensor for detecting the temperature inside the furnace heating enclosure, said method comprising the steps of:

bringing the temperature within the heating enclosure to a level not higher than the freezing point of water; and blowing a drying gas against the cover from outside of the heating furnace, at a rate sufficient to lower the dew point in the vicinity of the sample introduction opening to a level to substantially prevent frost from forming in the heating enclosure at the location of the sample introduction opening.

* * * * *